United States Patent
Adamy

(10) Patent No.: US 12,250,921 B2
(45) Date of Patent: Mar. 18, 2025

(54) ANIMAL LITTERS EXHIBITING ENHANCED ODOR REDUCTION PROPERTIES, AND RELATED METHODS

(71) Applicant: Church & Dwight Co., Inc., Princeton, NJ (US)

(72) Inventor: Steven T. Adamy, Lawrenceville, NJ (US)

(73) Assignee: Church & Dwight Co., Inc., Princeton, NJ (US)

( * ) Notice: Subject to any disclaimer, the term of this patent is extended or adjusted under 35 U.S.C. 154(b) by 922 days.

(21) Appl. No.: 17/278,503

(22) PCT Filed: Sep. 24, 2019

(86) PCT No.: PCT/IB2019/058107
§ 371 (c)(1),
(2) Date: Mar. 22, 2021

(87) PCT Pub. No.: WO2020/065540
PCT Pub. Date: Apr. 2, 2020

(65) Prior Publication Data
US 2022/0030824 A1    Feb. 3, 2022

Related U.S. Application Data

(60) Provisional application No. 62/736,365, filed on Sep. 25, 2018.

(51) Int. Cl.
*A01K 1/015*    (2006.01)
*A61L 9/014*    (2006.01)
(Continued)

(52) U.S. Cl.
CPC ............ *A01K 1/0154* (2013.01); *A61L 9/014* (2013.01); *B01D 53/04* (2013.01);
(Continued)

(58) Field of Classification Search
CPC ....... A01K 1/0154; A61L 9/014; B01D 53/04; B01D 2253/108; B01D 2257/406; B82Y 99/00
See application file for complete search history.

(56) References Cited

U.S. PATENT DOCUMENTS 3,641,095 A * 2/1972 Kiowsky et al. ...... B01J 20/183
502/68
3,816,330 A     6/1974 Havens et al.
(Continued)

FOREIGN PATENT DOCUMENTS

| EP | 1604792 | 9/2007 |
|---|---|---|
| KR | 100424788 B1 * | 3/2004 |
| KR | 101333778 B1 * | 11/2013 |

OTHER PUBLICATIONS

Kim KR101333778B1 English Translation w numbering (Year: 2013).*

(Continued)

*Primary Examiner* — Sally A Merkling
*Assistant Examiner* — Jordan W Taylor
(74) *Attorney, Agent, or Firm* — Church & Dwight Co., Inc.

(57) ABSTRACT

An animal litter composition having enhanced odor reduction properties, and a related method, are disclosed. The animal litter can include a zeolite-based liquid adsorbing material. The animal litter can also include a nanosilicate odor reducing agent that reduces an odor of litter waste, the animal litter composition having a total nanosilicate odor reducing agent content of about 0.5% by weight to about 13% by weight based on the total weight of the animal litter composition.

18 Claims, 10 Drawing Sheets

(51) Int. Cl.
*B01D 53/04* (2006.01)
*B82Y 99/00* (2011.01)

(52) U.S. Cl.
CPC .. *B01D 2253/108* (2013.01); *B01D 2257/406* (2013.01); *B82Y 99/00* (2013.01)

(56) References Cited

U.S. PATENT DOCUMENTS

| | | | |
|---|---|---|---|
| 4,437,429 A | 3/1984 | Goldstein et al. | |
| 4,683,318 A | 7/1987 | Deffeves et al. | |
| 5,143,023 A * | 9/1992 | Kuhns | A01K 1/0152 |
| | | | 119/173 |
| 6,436,384 B2 | 8/2002 | Santoiemmo | |
| 6,659,042 B2 | 12/2003 | Bloomer | |
| 7,429,421 B2 | 9/2008 | Greene et al. | |
| 7,879,350 B2 | 2/2011 | Macdonald et al. | |
| 8,720,375 B2 * | 5/2014 | Miller | A01K 1/0155 |
| | | | 119/173 |
| 9,314,544 B2 | 4/2016 | Catalan et al. | |
| 9,854,782 B2 | 1/2018 | Sogou et al. | |
| 2005/0084412 A1 | 4/2005 | Macdonald et al. | |
| 2005/0084438 A1 * | 4/2005 | Do | B01J 20/3217 |
| | | | 423/244.02 |
| 2010/0189595 A1 * | 7/2010 | Webster | A61L 9/014 |
| | | | 422/4 |
| 2011/0017143 A1 | 1/2011 | Matsuo et al. | |
| 2011/0174228 A1 * | 7/2011 | Liu | A01K 1/0154 |
| | | | 119/173 |
| 2012/0024235 A1 * | 2/2012 | Boxley | B01J 20/16 |
| | | | 119/171 |
| 2012/0202236 A1 * | 8/2012 | Jollez | A01K 1/0155 |
| | | | 435/28 |
| 2013/0189334 A1 | 7/2013 | Disalvo et al. | |
| 2015/0027381 A1 | 1/2015 | Bander et al. | |
| 2016/0165835 A1 | 6/2016 | Lipscomb et al. | |

OTHER PUBLICATIONS

Ludox® AS-40 (Silicas)—Grace—Technical Datasheet, search before Sep. 25, 2018 (Year: 2018).*
KR100424788B1 English Machine Translation (Year: 2004).*

* cited by examiner

ANIMAL LITTERS EXHIBITING ENHANCED ODOR REDUCTION PROPERTIES, AND RELATED METHODS

FIELD OF THE DISCLOSURE

The present disclosure relates to an adsorbent composition and its method of production, as well as its use as an animal litter. More particularly, the adsorbent composition is configured to enhance odor reduction.

BACKGROUND

Various types of litters have been used for many years in the area of pet care to provide a dedicated location for housebroken animals, such as cats, to urinate and defecate indoors. Litters generally can be formed of a liquid-absorbing material, such as clay, to provide for efficient absorption of urine. Litters further can include a variety of added materials, such as clumping aids, fragrances, and the like. The most commonly used litter box liquid-absorbing materials are inexpensive clays, such as calcined clays, that are safe and non-irritating to the animals, and that absorb substantial amounts of liquids. Other porous, solid litter box absorbent materials, that are used alone or in combination, include straw, sawdust, wood chips, wood shavings, porous polymeric beads, shredded paper, sand, bark, cloth, ground corn husks, and cellulose. Each of these absorbent materials has the advantage of low cost.

The entire contents of the litter box including the soiled and unsoiled liquid-absorbing materials will eventually be removed because of the offensive odor caused by the absorbed urine and feces in the liquid-absorbing materials in the litter box. Accordingly, there remains a need for improved animal litters that particularly exhibit enhanced odor reduction properties, while still remaining a lightweight and easy to dispose of litter.

SUMMARY OF THE DISCLOSURE

The present disclosure relates to animal litter compositions having enhanced odor reduction properties, and related methods. In some aspects, an animal litter composition may comprise a zeolite-based liquid adsorbing material; and a nanosilicate odor reducing agent that reduces an odor of litter waste, the animal litter composition having a total nanosilicate odor reducing agent content of about 0.5% by weight to about 13% by weight based on the total weight of the animal litter composition. In one or more embodiments, the animal litter may be further defined in relation to one or more of the following statements, which may be combined in any number or order.

The animal litter can include the zeolite-based liquid adsorbing material comprising clinoptilolite, ferrierite, chabazite, mordenite, or a combination thereof.

The animal litter can include the nanosilicate odor reducing agent that reduces the odor of ammonia ($NH_3$).

The animal litter can include the nanosilicate odor reducing agent being cationic.

The animal litter can further include an additive material including a binder, a preservative, a biocide, a de-dusting agent, a fragrance, a bicarbonate, a clump aid, or a combination thereof.

The animal litter can include the zeolite-based liquid adsorbing material defining channel dimensions having a channel area of 23.7 $Å^2$ or less.

The animal litter can include the zeolite-based liquid adsorbing material defining a void volume of about 50% or less.

The animal litter can include the zeolite-based liquid adsorbing material having a cation exchange capacity of 4.00 meq/g or less.

The animal litter can include the nanosilicate odor reducing agent defining a plurality of particles, each particle having an approximate particle size of 22 nm or less.

The animal litter can include the nanosilicate odor reducing agent being present as a coating on at least a portion of an outer surface of the zeolite-based liquid adsorbing material.

In some aspects, a method for producing an animal litter composition may comprise providing a zeolite-based liquid adsorbing material; and coating the zeolite-based liquid adsorbing material with a nanosilicate odor reducing agent that reduces an odor of litter waste, said coating being sufficient to provide the animal litter composition with a total nanosilicate odor reducing agent content of about 0.5% by weight to about 13% by weight based on the total weight of the animal litter composition. In one or more embodiments, the method may be further defined in relation to one or more of the following statements, which may be combined in any number or order.

The method can include providing clinoptilolite, ferrierite, chabazite, mordenite, or a combination thereof.

The method can include coating the zeolite-based liquid adsorbing material with a nanosilicate odor reducing agent that reduces the odor of ammonia ($NH_3$).

The method can include coating the zeolite-based liquid adsorbing material with a nanosilicate odor reducing agent that is cationic.

The method can further include mixing the zeolite-based liquid adsorbing material with an additive material including a binder, a preservative, a biocide, a de-dusting agent, a fragrance, a bicarbonate, a clump aid, or a combination thereof.

The method can include providing a zeolite-based liquid adsorbing material defining channel dimensions having a channel area of 23.7 $Å^2$ or less.

The method can include providing a zeolite-based liquid adsorbing material defining a void volume of about 50% or less.

The method can include providing a zeolite-based liquid adsorbing material having a cation exchange capacity of 4.00 meq/g or less.

The method can include coating the zeolite-based liquid adsorbing material with a nanosilicate odor reducing agent defining a plurality of particles, each particle having an approximate particle size of 22 nm or less.

The method can include coating the zeolite-based liquid adsorbing material with the nanosilicate odor reducing agent on at least a portion of an outer surface of the zeolite-based liquid adsorbing material.

The present disclosure thus includes, without limitation, the following embodiments:

Embodiment 1

An animal litter composition comprising: a zeolite-based liquid adsorbing material; and a nanosilicate odor reducing agent that reduces an odor of litter waste, the animal litter composition having a total nanosilicate odor reducing agent content of about 0.5% by weight to about 13% by weight based on the total weight of the animal litter composition.

Embodiment 2

The animal litter composition of any preceding embodiment, or any combination of preceding embodiments, wherein the zeolite-based liquid adsorbing material comprises clinoptilolite, ferrierite, chabazite, mordenite, or a combination thereof.

Embodiment 3

The animal litter composition of any preceding embodiment, or any combination of preceding embodiments, wherein the nanosilicate odor reducing agent reduces the odor of ammonia ($NH_3$).

Embodiment 4

The animal litter composition of any preceding embodiment, or any combination of preceding embodiments, wherein the nanosilicate odor reducing agent is cationic.

Embodiment 5

The animal litter composition of any preceding embodiment, or any combination of preceding embodiments, the animal litter composition further comprising an additive material including a binder, a preservative, a biocide, a de-dusting agent, a fragrance, a bicarbonate, a clump aid, or a combination thereof.

Embodiment 6

The animal litter composition of any preceding embodiment, or any combination of preceding embodiments, wherein the zeolite-based liquid adsorbing material defines channel dimensions having a channel area of 23.7 $Å^2$ or less.

Embodiment 7

The animal litter composition of any preceding embodiment, or any combination of preceding embodiments, wherein the zeolite-based liquid adsorbing material defines a void volume of about 50% or less.

Embodiment 8

The animal litter composition of any preceding embodiment, or any combination of preceding embodiments, wherein the zeolite-based liquid adsorbing material has a cation exchange capacity of 4.00 meq/g or less.

Embodiment 9

The animal litter composition of any preceding embodiment, or any combination of preceding embodiments, wherein the nanosilicate odor reducing agent defines a plurality of particles, each particle having an approximate particle size of 22 nm or less.

Embodiment 10

The animal litter composition of any preceding embodiment, or any combination of preceding embodiments, wherein the nanosilicate odor reducing agent is present as a coating on at least a portion of an outer surface of the zeolite-based liquid adsorbing material.

Embodiment 11

A method for producing an animal litter composition, the method comprising: providing a zeolite-based liquid adsorbing material; and coating the zeolite-based liquid adsorbing material with a nanosilicate odor reducing agent that reduces an odor of litter waste, said coating being sufficient to provide the animal litter composition with a total nanosilicate odor reducing agent content of about 0.5% by weight to about 13% by weight based on the total weight of the animal litter composition.

Embodiment 12

The method of any preceding embodiment, or any combination of preceding embodiments, wherein providing the zeolite-based liquid adsorbing material comprises providing clinoptilolite, ferrierite, chabazite, mordenite, or a combination thereof.

Embodiment 13

The method of any preceding embodiment, or any combination of preceding embodiments, wherein coating the zeolite-based liquid adsorbing material with the nanosilicate odor reducing agent comprises coating the zeolite-based liquid adsorbing material with a nanosilicate odor reducing agent that reduces the odor of ammonia ($NH_3$).

Embodiment 14

The method of any preceding embodiment, or any combination of preceding embodiments, wherein coating the zeolite-based liquid adsorbing material with the nanosilicate odor reducing agent comprises coating the zeolite-based liquid adsorbing material with a nanosilicate odor reducing agent that is cationic.

Embodiment 15

The method of any preceding embodiment, or any combination of preceding embodiments, the method further comprising mixing the zeolite-based liquid adsorbing material with an additive material including a binder, a preservative, a biocide, a de-dusting agent, a fragrance, a bicarbonate, a clump aid, or a combination thereof.

Embodiment 16

The method of any preceding embodiment, or any combination of preceding embodiments, wherein providing the zeolite-based liquid adsorbing material comprises providing a zeolite-based liquid adsorbing material defining channel dimensions having a channel area of 23.7 $Å^2$ or less.

Embodiment 17

The method of any preceding embodiment, or any combination of preceding embodiments, wherein providing the zeolite-based liquid adsorbing material comprises providing a zeolite-based liquid adsorbing material defining a void volume of about 50% or less.

Embodiment 18

The method of any preceding embodiment, or any combination of preceding embodiments, wherein providing the zeolite-based liquid adsorbing material comprises providing a zeolite-based liquid adsorbing material having a cation exchange capacity of 4.00 meq/g or less.

Embodiment 19

The method of any preceding embodiment, or any combination of preceding embodiments, wherein coating the zeolite-based liquid adsorbing material with the nanosilicate odor reducing agent comprises coating the zeolite-based liquid adsorbing material with a nanosilicate odor reducing agent defining a plurality of particles, each particle having an approximate particle size of 22 nm or less.

Embodiment 20

The method of any preceding embodiment, or any combination of preceding embodiments, wherein coating the zeolite-based liquid adsorbing material with the nanosilicate odor reducing agent comprises coating the zeolite-based liquid adsorbing material with the nanosilicate odor reducing agent on at least a portion of an outer surface of the zeolite-based liquid adsorbing material.

These and other features, aspects, and advantages of the present disclosure will be apparent from a reading of the following detailed description together with the accompanying drawings, which are briefly described below. The present disclosure includes any combination of two, three, four, or more features or elements set forth in this disclosure or recited in any one or more of the claims, regardless of whether such features or elements are expressly combined or otherwise recited in a specific embodiment description or claim herein. This disclosure is intended to be read holistically such that any separable features or elements of the disclosure, in any of its aspects and embodiments, should be viewed as intended to be combinable, unless the context of the disclosure clearly dictates otherwise.

BRIEF DESCRIPTION OF THE DRAWINGS

Figure 1:
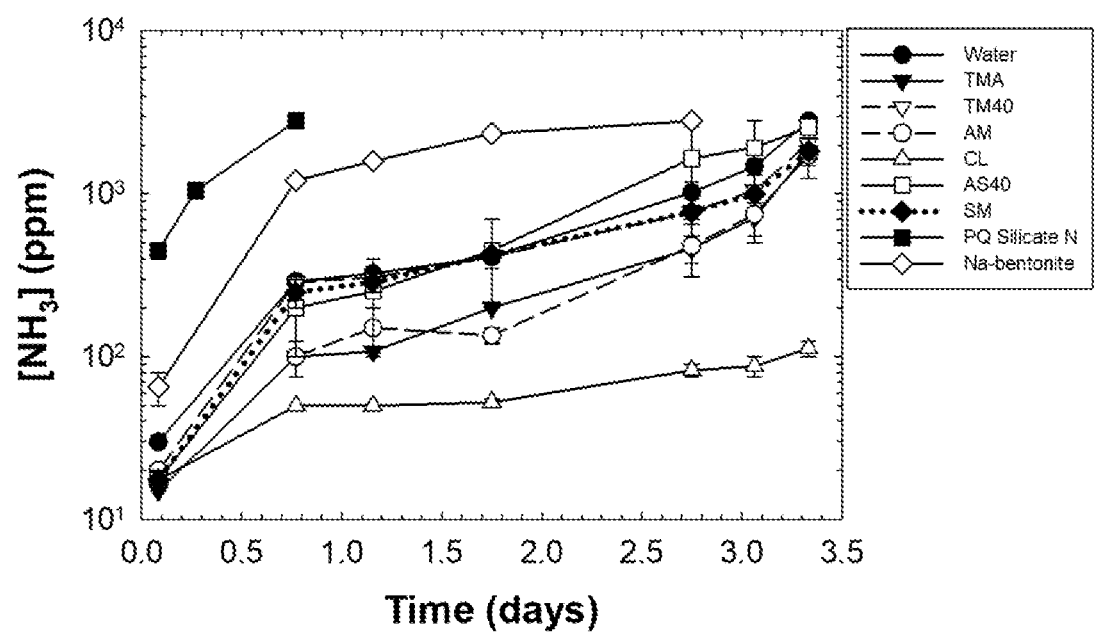
Figure 2:
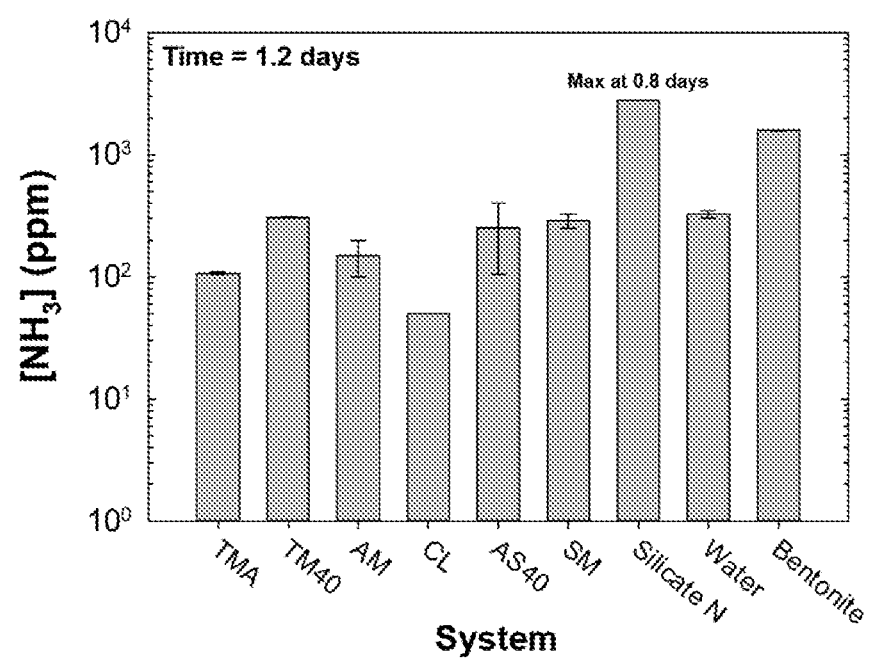
Figure 3:
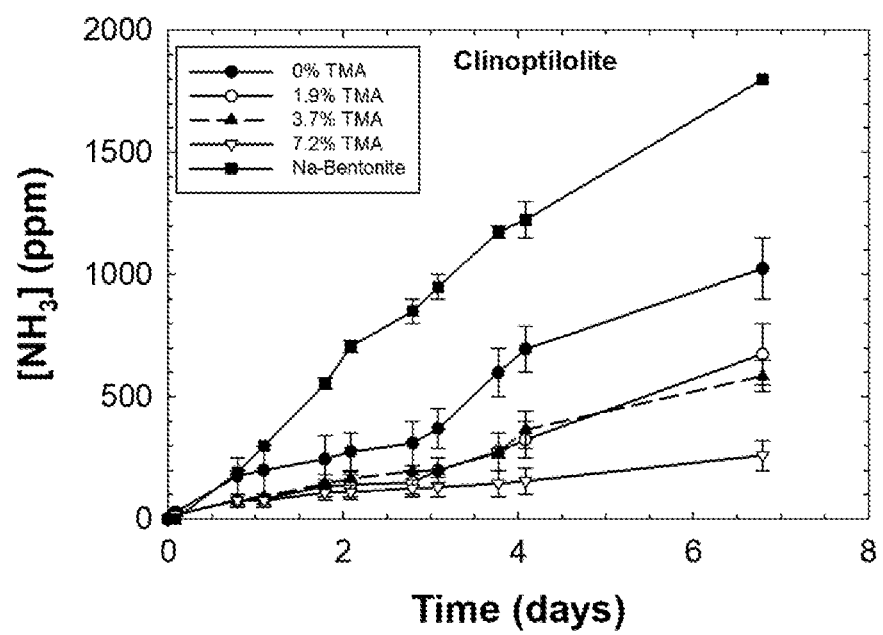
Figure 4:
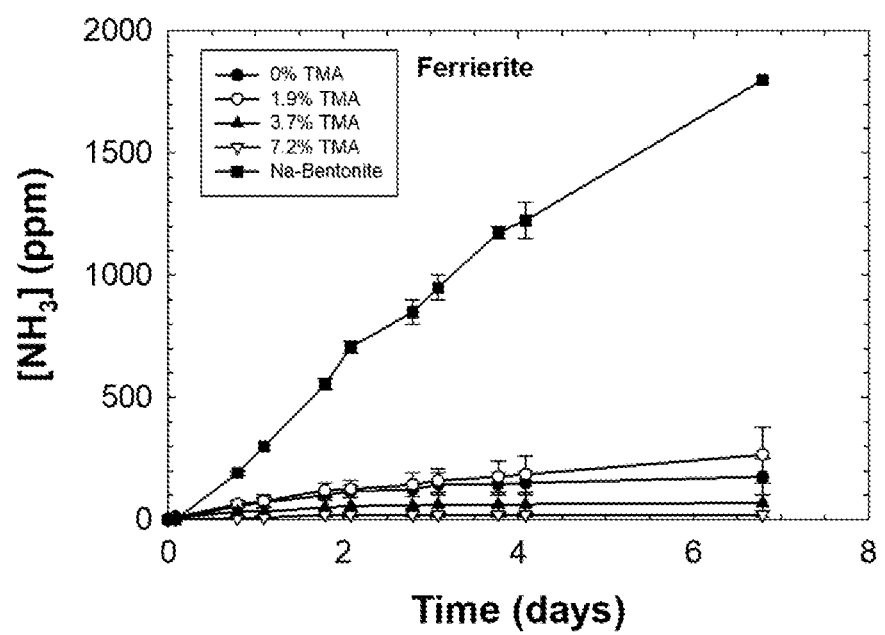
Figure 5:
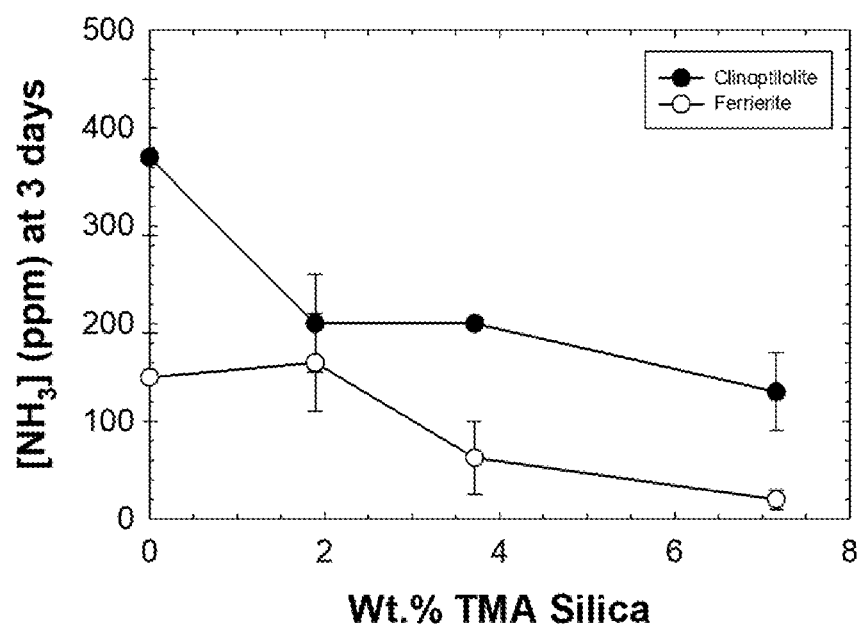
Figure 6:
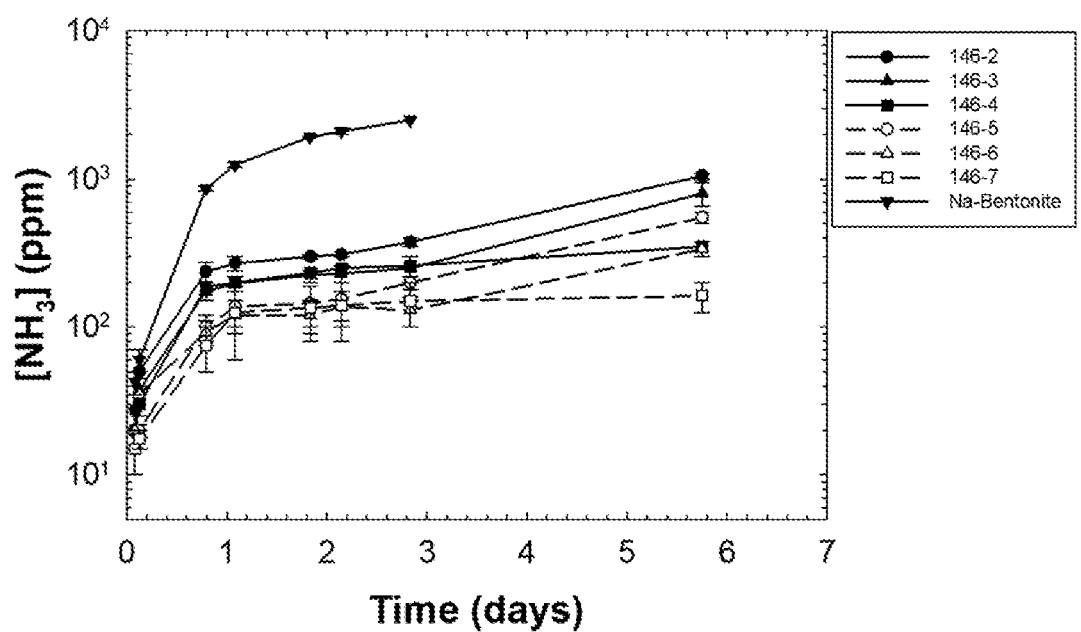
Figure 7:
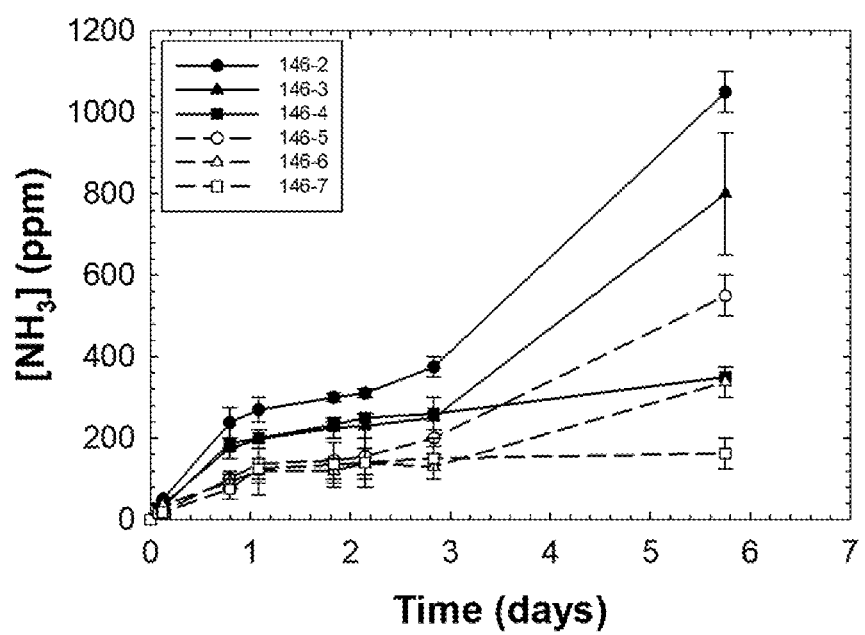
Figure 8:
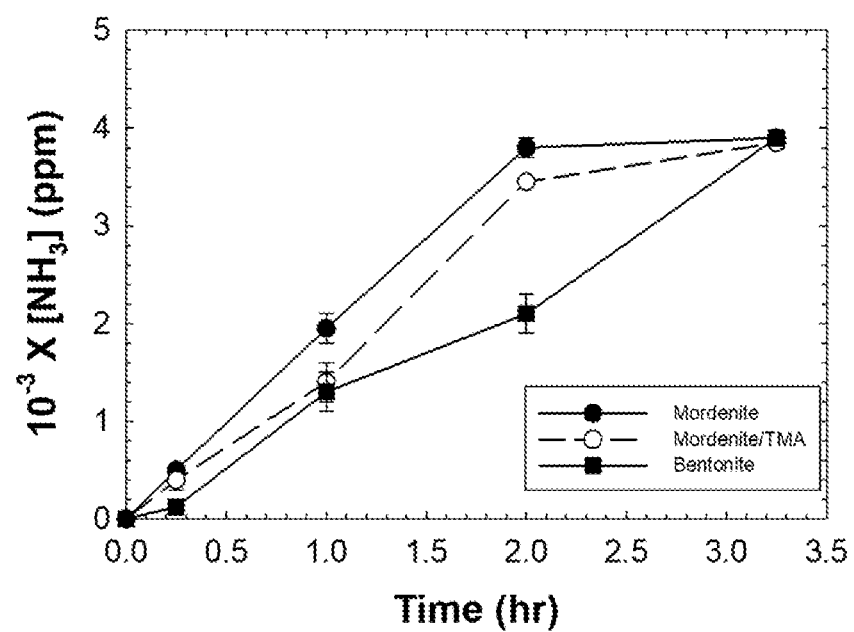
Figure 9:
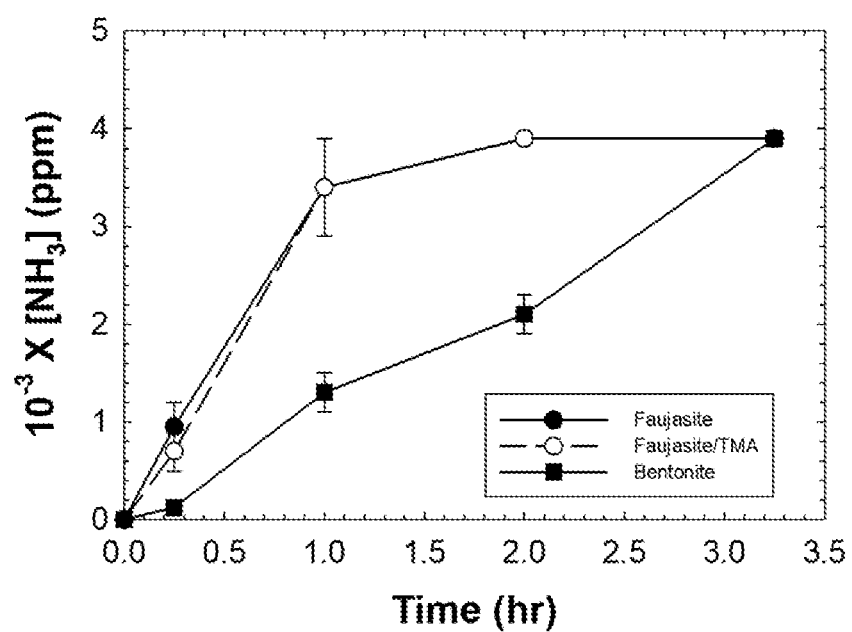
Figure 10:
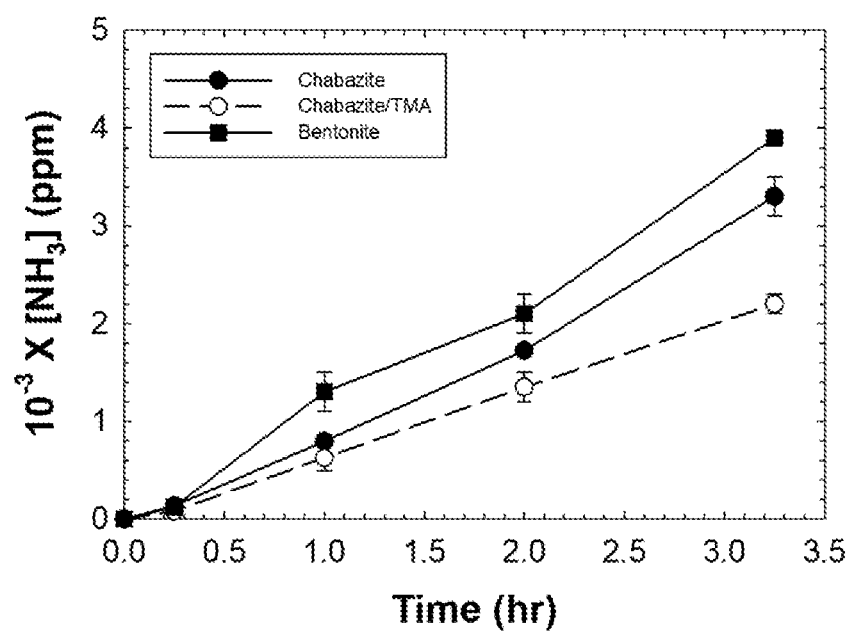

Having thus described the disclosure in general terms, reference will now be made to the accompanying drawings, which are not necessarily drawn to scale, and wherein:

FIG. 1 illustrates a graphical representation of a comparison of levels of $NH_3$ generated as a function of time according to an example aspect of the present disclosure;

FIG. 2 illustrates a graphical representation of a comparison of levels of $NH_3$ at 1.2 days according to an example aspect of the present disclosure;

FIG. 3 illustrates a graphical representation of a comparison of levels of $NH_3$ generated as a function of time for systems containing clinoptilolite according to an example aspect of the present disclosure;

FIG. 4 illustrates a graphical representation of a comparison of levels of $NH_3$ generated as a function of time for systems containing ferrierite according to an example aspect of the present disclosure;

FIG. 5 illustrates a graphical representation of a comparison of levels of $NH_3$ at three days for systems containing ferrierite and clinoptilolite according to an example aspect of the present disclosure;

FIG. 6 illustrates a graphical representation of a comparison of levels of $NH_3$ generated as a function of time for each of the litter systems, including Na-Bentonite, according to an example aspect of the present disclosure;

FIG. 7 illustrates a graphical representation of a comparison of levels of $NH_3$ generated as a function of time for each of the litter systems according to an example aspect of the present disclosure;

FIG. 8 illustrates a graphical representation of a comparison of levels of $NH_3$ generated as a function of time for systems containing mordenite according to an example aspect of the present disclosure;

FIG. 9 illustrates a graphical representation of a comparison of levels of $NH_3$ generated as a function of time for systems containing faujasite according to an example aspect of the present disclosure; and FIG. 10 illustrates a graphical representation of a comparison of levels of $NH_3$ generated as a function of time for systems containing chabazite according to an example aspect of the present disclosure.

DETAILED DESCRIPTION OF THE DISCLOSURE

The present disclosure now will be described more fully hereinafter with reference to specific embodiments and particularly to the various drawings provided herewith. Indeed, the disclosure may be embodied in many different forms and should not be construed as limited to the embodiments set forth herein; rather, these embodiments are provided so that this disclosure will satisfy applicable legal requirements. As used in the specification, and in the appended claims, the singular forms "a," "an," "the," include plural referents unless the context clearly dictates otherwise.

The present disclosure relates to a zeolite-based animal litter exhibiting enhanced odor reduction properties; specifically, odor reduction properties with regard to ammonia ($NH_3$). Ammonia ($NH_3$) may be produced from the metabolism of animals when urea is broken down. $NH_3$ may then be eliminated as urine, which has an offensive odor. Thus, the focus of this invention is to enhance the odor reduction properties of animal litters by providing an animal litter composition comprising a zeolite-based liquid adsorbing material and a nanosilicate odor reducing agent that reduces an odor of litter waste (e.g., $NH_3$). It has been found according to the present disclosure that the inclusion of a defined amount of at least one nanosilicate odor reducing agent (e.g., silica nanoparticles) to a zeolite-based liquid adsorbing material is surprisingly effective in enhancing odor reduction properties of the zeolite-based animal litter composition when it is wetted, i.e., by animal urine and feces. Additionally, the animal litter composition described herein can include additive materials including binders, preservatives, biocides, de-dusting agents, fragrances, bicarbonates, clump aids, and the like, to further enhance the odor reduction properties of the animal litter composition.

A zeolite-based liquid adsorbing material for use in an animal litter composition as described herein can include any such material previously recognized as useful in forming animal litters. Preferably, the zeolite-based liquid adsorbing material is a zeolite having a high selectivity for the adsorption of cations, e.g., $NH_4^+$, $Ca^{2+}$, and $K^+$, as well as polar molecules such as $H_2O$ and $NH_3$. For example, a zeolite-based liquid adsorbing material such as clinoptilolite, ferrierite, chabazite, mordenite, or a combination thereof, can be used in the present animal litter composition.

In one or more embodiments, the performance of the present animal litter composition can relate to one or more properties of the zeolite-based liquid adsorbing material apart from its ability to adsorb liquid. In some embodiments, performance can be improved through use of a zeolite-based liquid adsorbing material defining a void volume of about 50% or less. Void volume (or void fraction) refers to the fraction of the overall volume of a porous material that is defined by pores, channels, or other void spaces and is calculated as the volume of the void space divided by the total volume of the material. A void volume or void fraction may be determined via mercury injection. A sample may be placed in a pool of mercury in equilibrium with a certain pressure of gas (e.g., $N_2$). A volume of mercury displaced by the sample may provide the bulk volume. The pressure of the gas may then be increased, which may cause the mercury to penetrate the voids in the sample. The liquid may then displace in the opposite manner since it may enter the voids. The negative displacement may provide a measure of the void volume. For example, suitable zeolites may define a void volume of 47% or less, 34% or less, 28% or less, etc. Preferably, void volume can be in the range of about 1% to about 50%, about 5% to about 45%, or about 10% to about 40%.

In some other embodiments, performance can be improved through use of a zeolite-based liquid adsorbing material defining a specific cation exchange capacity (CEC). CEC can refer to the amount of positive charge that can be exchanged per mass of the material. The CEC may be calculated by noting the number of exchangeable cations in the unit cell (n) and dividing by the unit cell atomic mass ($M_{cell}$ in units of g). With CEC expressed as meq/g, this is $$CEC(meq/g) = (n/M_{cell}) \times 1000$$

For example, it can be useful to utilize a zeolite material having a CEC of about 4.00 milliequivalents per gram (meq/g) or less. For example, suitable zeolites may define a cation exchange capacity of about 3.39 meq/g or less, about 3.84 meq/g or less, about 2.33 meq/g or less, about 2.29 meq/g or less, about 2.16 meq/g or less, etc. CEC preferably can be in a range of about 1.0 meq/g to about 4.0 meq/g, about 1.25 meq/g to about 3.5 meq/g, or about 1.5 meq/g to about 3.0 meq/g. In some still further embodiments, performance can be improved though use of a zeolite-based liquid adsorbing material exhibiting defined channel dimensions. For example, suitable zeolite-based liquid adsorbing materials can define channel dimensions, where the channel dimensions can be about 3.9× about 5.4 Å, about 4.3× about 5.5 Å, about 3.7× about 4.2 Å, or about 2.9× about 5.7 Å. In some even further embodiments, the channel dimensions have a resulting channel area, such that the channel area of each suitable zeolite-base liquid adsorbing material is the product of the channel dimensions. For example, suitable zeolite-based liquid adsorbing materials can define a channel area of 21.1 Å$^2$, 23.7 Å$^2$, 14.3 Å$^2$, or 16.5 Å$^2$. It has been found that channel area of a zeolite may be related to the ability of the zeolite to enhance odor reduction in combination with treatment of the zeolite with a nanosilicate odor reducing agent. Specifically, a ratio of a channel area of a zeolite to a cross-sectional area of $NH_3$ molecules (e.g., litter waste that is desirable to reduce the odor of) may be used as a metric to determine the suitability of a zeolite for reducing an odor of said litter waste. The area of $NH_3$ may be determined based on the cross-sectional diameter of an $NH_3$ molecule, calculated from the associated van der Waals volume. With the volume equal to 22.0 Å$^3$, the associated molecular diameter d can be calculated to be 3.5 Å. The cross-sectional area of $NH_3$ may then be determined from the formula for an area of a circle ($\pi(d/2)^2$) to be 9.6 Å$^2$. Accordingly, the ratio of the channel area of the zeolite to the cross-sectional area of $NH_3$ may be about 2.2, about 2.5, about 1.6, or about 1.7. It has been determined that a zeolite having a ratio of about 2.5 or below may be exhibit enhanced odor reduction properties, where such properties may be enhanced further with treatment with a nanosilicate odor reducing agent.

The amount of the zeolite-based liquid adsorbing material used in the present animal litter composition can vary. For example, the zeolite-based liquid adsorbing material can form about 14% by weight to about 99.5% by weight of the composition. In further embodiments, the amount of the zeolite-based liquid adsorbing material in the animal litter composition can be about 20% by weight to about 94% by weight, about 25% by weight to about 90% by weight, about 30% by weight to about 80% by weight, or about 35% by weight to about 55% by weight based on the total weight of the composition. Preferably, the zeolite-based liquid adsorbing material forms about 88% to about 99.5% by weight of the composition.

The animal litter composition also includes a nanosilicate odor reducing agent that is effective in reducing an odor of litter waste, such as the $NH_3$ present in animal (feline) urine. The amount of nanosilicate odor reducing agent present in the animal litter composition can vary based upon one or more characteristics of the further components of the composition. In some embodiments, the total amount nanosilicate odor reducing agent in the animal litter composition can be about 0.5% by weight to about 13% by weight, about 1.25% by weight to about 7.5% by weight, about 1.5% by weight to about 7% by weight, about 1.6% by weight to about 6.5% by weight, or about 1.7% by weight to about 6% by weight based on the total weight of the animal litter composition. In some embodiments, particularly beneficial results can be achieved when the total nanosilicate odor reducing agent content is greater than 1% by weight, specifically greater than 1.25% by weight, and more specifically greater than 1.5% by weight based on the total weight of the animal litter composition. The maximum amount of nanosilicate odor reducing agent present can vary, and preferably is no greater than 13% by weight, no greater than 9% by weight, or no greater than 8% by weight based on the total weight of the animal litter composition.

In some embodiments, the total amount of nanosilicate odor reducing agent present in the animal litter composition may be configured to be determined relative to the quantity of the zeolite-based liquid adsorbing material by weight in the animal litter composition. In some aspects, it has surprisingly been found that odor reduction may be enhanced at between about 2% and about 4% nanosilicate odor reducing agent content by weight, based on the total weight of the animal litter composition, depending on the zeolite-based liquid adsorbing material used therewith. Accordingly, in some embodiments, the amount of nanosilicate odor reducing agent present can be varied by varying the quantity of zeolite-based liquid adsorbing material.

Several different types of nanosilicate odor reducing agents, such as silica nanoparticles, may be suitable according to the present disclosure. For example, silica nanoparticles such as LUDOX® TM 40, LUDOX® AM, LUDOX® CL, LUDOX® AS-40, LUDOX® CL-X, LUDOX® TMA, LUDOX® SM, which are all commercially available from W.R. Grace & Co., Columbia MD, and the like, may be suitable. The type of nanosilicate odor reducing agents that are suitable for the present disclosure particularly may have a specific counterion and/or approximate particle size of the nanosilicate odor reducing agent selected. The counterion or ion that accompanies an ionic species in order to maintain electric neutrality may be characterized based on the interaction of the nanosilicate odor reducing agent with $NH_3$ and/or by the zeolite-based liquid adsorbing material upon which the nanosilicate odor reducing agent is mixed therewith. Therefore, the type of nanosilicate odor reducing agent selected preferably may be a nanosilicate that is overall cationic, a nanosilicate having a $Na^+$ counterion, a nanosilicate having a $NH_4^+$ counterion, or a deionized nanosilicate. In some other aspects, the type of nanosilicate odor reducing agents used may define a plurality of particles, wherein the particles have an average particle size of about 22 nm or less. For example, the nanosilicate odor reducing agents may define a plurality of particles having an average particle size of about 22 nm or less, about 15 nm or less, about 12 nm or less, about 10 nm or less, or about 7 nm or less. Average nanosilicate particle size particularly may be in a range of about 2 nm to about 22 nm, about 3 nm to about 20 nm, or about 5 nm to about 15 nm. In some embodiments, for example, particularly beneficial results can be achieved when the nanosilicate odor reducing agent with an $Na^+$ counterion defines a plurality of particles having an average particle size of about 12 nm. In another embodiment, for example, particularly beneficial results can be achieved when the nanosilicate odor reducing agent with a deionized particle defines a plurality of particles having an average particle size of 22 nm. Therefore, the suitability of the average particle size for the nanosilicate odor reducing agent may depend on the counterion or type of ionic species thereof.

In addition to the foregoing, the ability of a litter composition according to the present disclosure to exhibit enhanced odor reduction may also be affected by a type of additive material used in the animal litter composition, or a ratio of the additive material to the zeolite-based liquid adsorbing material and the nanosilicate odor reducing agent. For example, a ratio of zeolite-based liquid adsorbing material to additive (i.e., PPN4000 guar) is 20:1.

In one or more embodiments, an additive material may include any material added to the animal litter composition disclosed herein other than the zeolite-based liquid adsorbing material and the nanosilicate odor reducing agent. In one or more embodiments, for example, the additive material may include one or more clump aid, or clump enhancing material. Description of suitable clump aids are provided in U.S. Pat. No. 8,720,375 to Miller et al., the disclosure of which is incorporated herein by reference. Useful clump aids are those materials suitable to promote adhesion of the fine size particles of litter granules to each other as well as adhesion of the particles to form agglomerates when wetted. Preferably, the clump aid allows the formation of a gelled agglomerate when exposed to a liquid, such as animal urine. A clump aid may be provided in admixture (e.g., in particle form) with the further materials forming the animal litter. In some embodiments, the clump aid can be provided as a coating on at least a portion of the other particles forming the animal litter (e.g., as a coating on at least a portion of the zeolite-based liquid adsorbing material). Such coatings may be provided by any known method, such as spraying.

Non-limiting examples of materials suitable for use as a clump aid include naturally occurring polymers (e.g., naturally occurring starches, water soluble polysaccharides, and gums), semisynthetic polymers (e.g., cellulose derivatives, such as carboxymethyl cellulose), and sealants. Exemplary clump aids include amylopectins, natural gums (e.g., guar gum), and sodium carboxymethylcellulose. The amount of any clump aid that is present in the animal litter composition can vary based upon the total composition. In some embodiments, a clump aid can be present in a total amount of 0.1% by weight to about 6% by weight, about 0.2% by weight to about 5.5% by weight, about 0.3% by weight to about 5% by weight, or about 0.5% by weight to about 4% by weight.

In addition to the foregoing, one or more further materials may be included in the present animal litter composition. Specifically, any conventional litter additive may be included to the extent that there is no interference with the ability of the litter composition to provide the useful effect of reduced adherence to surfaces when wetted. Non-limiting examples of additional additive materials that may be used include binders, preservatives, such as biocides (e.g., benzisothiazolinone, methylisothiazolone), de-dusting agents, fragrances, bicarbonates, and combinations thereof. Each of the foregoing materials separately may be included in any amount up to about 6% by weight, up to about 2% by weight, up to about 1% by weight, or up to about 0.5% by weight, such as about 0.01% by weight to about 5% by weight, to about 4% by weight, to about 3% by weight, to about 2% by weight, or to about 1% by weight based on the total weight of the animal litter composition. Further, it is understood that any one or more of such materials may be expressly excluded from the present animal litter composition.

In one or more embodiments, an animal litter composition according to the present disclosure providing enhanced odor reduction properties include components in the ranges shown in TABLE 1 below.

TABLE 1

| Ingredients | Percentage (%) |
| --- | --- |
| Zeolite-based liquid adsorbing material | qs to 100% |
| Nanosilicate odor reducing agent | 0.5 to 13% |
| Clump aids | 0 to 6% |
| Fragrance | 0 to 2% |
| Preservatives | 0 to 0.5% |
| Bicarbonate | 0 to 0.5% |

The advantages of an animal litter waste composition formulated using the exemplary formulation include enhanced odor reduction properties, easier litter waste removal, full clump removal, etc. The animal litter compositions described herein may be used for a wide variety of animals and birds, e.g., uncaged household pets, such as cats and dogs, particularly puppies too young to be walked; caged pets, such as hamsters, gerbils and rabbits; caged laboratory animals, such as guinea pigs, mice, rats and monkeys; animals raised for fur, such as mink; barnyard birds, such as chickens, ducks and geese; and pet birds, such as parrots, parakeets, canaries and pigeons. The compositions of this invention are particularly suitable for use as cat litters.

A method for producing an animal litter composition is also disclosed herein. The method may comprise a first step of providing a zeolite-based liquid adsorbing material. The method may comprise a second step of coating the zeolite-based liquid adsorbing material with a nanosilicate odor reducing agent that reduces an odor of litter waste, said coating being sufficient to provide the animal litter composition with a total nanosilicate odor reducing agent content of about 0.5% by weight to about 13% by weight based on the total weight of the animal litter composition.

Other methods for incorporating the nanosilicate material into the mixture with the zeolite and other materials may entail preparation of a composition containing all components, such that enough liquid is added to dry ingredients that the resulting composition is cohesive and is extrudable.

The mixture can then be extruded into extrudate of appropriate diameter, for example 1 to 5 mm. The extrudate can further be chopped into smaller segments, or spheronized using a spheronizer. The resulting pellets can then be dried via a fluidized bed or oven.

Example 1

Testing was carried out by preparing agglomerated litter. Clinoptilolite powder (+20/−30 mesh) was mixed with guar powder (Rantec PPN4000). The mixture was placed in a rotating drum agglomerator. While rotating the mixture at a speed of about 55 RPM, the powder was sprayed with either water (control) or with a 9% (w/w) dispersion of nanosilicate odor reducing agents. The moist mixture was then removed from the drum, placed into a metal pan, and dried in a 60° C. oven overnight.

TABLE 2 illustrates the specific compositions of each sample. The samples included the different nanosilicate odor reducing agents, water, and a traditional sodium silicate solution (Silicate N from PQ). LUDOX® samples are identified by their tradenames, but all represent 9.0% (w/w) dispersions in water:

TABLE 2

| 5099-30 | Clinoptiolite (g) | PPN 4000 (g) | Water (g) | TMA 9.0% (g) | TM40 9.0% (g) | AM 9.0% (g) | CL 9.0% (g) | AS40 9.0% (g) | SM 9.0% (g) | PQ silicate N 9.0% (g) |
|---|---|---|---|---|---|---|---|---|---|---|
| 1 | 150 | 7.5 | 67.5 | | | | | | | |
| 2 | 150 | 7.5 | | 67.5 | | | | | | |
| 3 | 150 | 7.5 | | | 67.5 | | | | | |
| 4 | 150 | 7.5 | | | | 67.5 | | | | |
| 5 | 150 | 7.5 | | | | | 67.5 | | | |
| 6 | 150 | 7.5 | | | | | | 67.5 | | |
| 7 | 150 | 7.5 | | | | | | | 67.5 | |
| 8 | 150 | 7.5 | | | | | | | | 67.5 |

The compositions were formulated such that each of samples 2-8 contained 3.7% nanosilicate odor reducing agents, 91.7% clinoptilolite, and 4.6% guar gum on dry bases. Sample 1 contained 95.2% clinoptilolite and 4.8% guar gum on a dry basis. The litters were evaluated for odor efficacy by placing 40.0 g of each litter in a 250 mL Erlenmeyer flask. To the litter was added 20.0 mL of cat urine, previously collected and pasteurized, less than one month old (kept refrigerated). The flask was then stoppered with a 1-hole Neoprene stopper, through which was placed a Draeger tube sensitive to $NH_3$. The flasks were incubated at room temperature, and levels of $NH_3$ generated were checked daily. Sodium bentonite was also evaluated for comparison, except that 100.0 g of bentonite was used in the flask in order to represent about the same volume as the agglomerated litters. All trials were run in duplicate.

FIG. 1 provides a graphical representation of the levels of $NH_3$ generated as a function of time for each of the samples in TABLE 2. Note the y-axis ([$NH_3$]) is a log scale. The data in FIG. 1 illustrates that LUDOX® CL was most effective in mitigating $NH_3$ production. This may have been due to its cationic nature, which could have inhibited bacterial growth. Next efficacious were the LUDOX® TMA (nonionic, 22 nm) and LUDOX® AM ($Na^+$ counterion, 12 nm) systems. Systems LUDOX® TM 40 ($Na^+$, 22 nm), LUDOX® SM ($Na^+$, 7 nm), and LUDOX® AS-40 ($NH_4^+$, 22 nm) showed about the same efficacy as treatment with water. The sodium bentonite performed worse than all of the nanosilicate systems. Most interesting was the observation that application of the silicate N made the odor mitigation efficacy much worse than all other systems including water only.

For clarity, values of $NH_3$ at 1.2 days were compared in FIG. 2. Note that the Silicate N systems had reached the maximum level of $NH_3$ that could be measured (around 2800 ppm) after 0.8 days. The data in FIGS. 1 and 2 therefore illustrates that treatment of the zeolite-based liquid adsorbing material with a nanosilicate odor reducing agent improved odor mitigation efficacy of $NH_3$.

Example 2

A series of studies were performed in order to investigate the effect of nanosilicate concentration on odor reduction. A series of samples were prepared in a manner similar to those in EXAMPLE 1, except the quantity of nanosilicate odor reducing agent was varied from 0 to 8.3% LUDOX® TMA (dry basis). Samples with clinoptilolite and ferrierite (−14/+40 mesh) were prepared, as indicated below in TABLE 3.

TABLE 3

| 5099-19 | Clin-optio lite (g) | Ferrier-ite (g) | PPN 4000 (g) | Water (g) | TMA 4.5% (g) | TM40 9.0% (g) | TMA 18.0% (g) |
|---|---|---|---|---|---|---|---|
| 1 | 150 | | 7.5 | 67.5 | | | |
| 2 | 150 | | 7.5 | | 67.5 | | |
| 3 | 150 | | 7.5 | | | 67.5 | |
| 4 | 150 | | 7.5 | | | | 67.5 |
| 5 | | 150 | 7.5 | 67.5 | | | |
| 6 | | 150 | 7.5 | | 67.5 | | |
| 7 | | 150 | 7.5 | | | 67.5 | |
| 8 | | 150 | 7.5 | | | | 67.5 |

LUDOX® TMA was selected as it showed the best level of performance in EXAMPLE 1, except for LUDOX® CL. In this test, it was intended that only the effect of the nanosilicate odor reducing agent be explored, without any possible effect of the (antimicrobial) cationic group. Once dried, the compositions above netted the following levels of ingredients, as illustrated below in TABLE 4.

TABLE 4

| 50999-19 | % Clinoptilolite | % Ferrierite | % PPN4000 | % Silica |
|---|---|---|---|---|
| 1 | 95.238 | 0.000 | 4.762 | 0.000 |
| 2 | 93.436 | 0.000 | 4.672 | 1.892 |
| 3 | 91.701 | 0.000 | 4.585 | 3.714 |

TABLE 4-continued

| 50999-19 | % Clinoptilolite | % Ferrierite | % PPN4000 | % Silica |
|---|---|---|---|---|
| 4 | 88.417 | 0.000 | 4.421 | 7.162 |
| 5 | 0.000 | 95.238 | 4.762 | 0.000 |
| 6 | 0.000 | 93.436 | 4.672 | 1.892 |
| 7 | 0.000 | 91.701 | 4.585 | 3.714 |
| 8 | 0.000 | 88.417 | 4.421 | 7.162 |

The samples were evaluated for mitigation of $NH_3$ odor as described in EXAMPLE 1. Shown in FIG. 3 are plots of $NH_3$ levels generated as a function of time for systems containing clinoptilolite. As before a Na-bentonite sample was included, though Na-bentonite samples were used merely for comparison purposes as to their inferiority in reducing odor.

The data showed that increasing the level of LUDOX® TMA nanosilica decreased $NH_3$ levels. Shown in FIG. 4 are plots of $NH_3$ levels generated as a function of time for systems containing ferrierite. Trends in odor reduction were similar to trends in the clinoptilolite system. Comparing odor levels in the clinoptilolite and ferrierite systems at three days, reductions in odor with increasing nanosilicate level can be seen in FIG. 5. As is shown in FIG. 5, ferrierite was more effective in reducing odor as compared with clinoptilolite systems.

Example 3

Compositions were prepared similarly to those in EXAMPLES 1 and 2, by spraying with either water or a 4.5% dispersion of LUDOX® TMA in water. The compositions are summarized in TABLE 5.

TABLE 5

| 5052-146 | Clinoptiolite (g) | Ferrierite (g) | PPN 4000 (g) | Water (g) | TMA 4.5% (g) |
|---|---|---|---|---|---|
| 2 | 100 | | 5 | 45 | |
| 3 | 50 | 50 | 5 | 45 | |
| 4 | | 100 | 5 | 45 | |
| 5 | 100 | | 5 | | 45 |
| 6 | 50 | 50 | 5 | | 45 |
| 7 | | 100 | 5 | | 45 |

The samples were dried as noted in EXAMPLES 1 and 2. Experiments to assess odor mitigation from cat urine were set up as described in EXAMPLES 1 and 2. Shown in FIG. 6 are results of odor measurements generated as a function of time for each of the litter systems. As in EXAMPLES 1 and 2, results are also presented for a sodium bentonite system.

All formulated systems displayed better odor reduction efficacy than sodium bentonite. In FIG. 7, it can be seen that all systems treated with nanosilicate odor reducing agent performed better than corresponding systems without nanosilicate odor reducing agent added to the zeolite-based liquid adsorbing material.

Example 4

Similar to EXAMPLES 1-3, samples of agglomerated litter material were prepared by mixing zeolite powder with guar powder (Rantec PPN4000) and placing the mixture in a rotating drum agglomerator. While rotating the mixture at a speed of about 55 RPM, the powder was sprayed with either water (control) or with an 18% (w/w) dispersion of nanosilicate odor reducing agents (LUDOX® TMA). The moist mixture was then removed from the drum, placed into a metal pan, and dried in a 60° C. oven overnight. The different zeolite powders and properties of each zeolite powder are illustrated below in TABLE 6.

TABLE 6

| Mineral | Unit Cell Formula | Void volume (%) | Channel Dimensions (Å) | Cation Exchange Capacity (meq/g) |
|---|---|---|---|---|
| Clinoptilolite | $(Na_3K_3)$ $(Al_6Si_{30}O_{72})\cdot 24H_2O$ | 34 | 3.9 × 5.4 | 2.16 |
| Ferrierite | $(Na_2Mg_2)$ $(Al_6Si_{30}O_{72})\cdot 18H_2O$ | 28 | 4.3 × 5.5 | 2.33 |
| Chabazite | $(Na_2Ca)_6$ $(Al_{12}Si_{24}O_{72})\cdot 40H_2O$ | 47 | 3.7 × 4.2 | 3.84 |
| Mordenite | $(Na_8)$ $(Al_8Si_{40}O_{96})\cdot 24H_2O$ | 28 | 2.9 × 5.7 6.7 × 7.0 | 2.29 |
| Faujasite | $(Na_{58})$ $(Al_{58}Si_{134}O_{384})\cdot 240H_2O$ | 47 | 7.4 | 3.39 |

Shown in TABLE 7 are the specific compositions of each sample prepared. Levels of water and 18% LUDOX® TMA (active basis) were varied between the different zeolites, since the zeolites exhibited different water absorption capabilities. Also shown are resulting % levels of LUDOX® TMA silica calculated on a dry basis:

TABLE 7

| Sample 5099-97- | Mordenite (Fine powder) | Faujasite (Fine powder) | Chabazite (14X40 mesh) | Rantex PPN 4000 | DI Water | 18% TMA silica (w/w) | % TMA silica |
|---|---|---|---|---|---|---|---|
| 1 | 150.00 | | | 7.50 | 119.87 | | 0.00 |
| 2 | 150.00 | | | 7.50 | | 119.87 | 12.05 |
| 3 | | 150.00 | | 7.50 | 124.88 | | 0.00 |
| 4 | | 150.00 | | 7.50 | | 124.88 | 12.49 |
| 5 | | | 150.00 | 7.50 | 70.4 | | 0.00 |
| 6 | | | 150.00 | 7.50 | | 70.4 | 7.45 |

The litters were evaluated for odor efficacy by placing 40.0 g of each litter in a 250 mL Erlenmeyer flask. To the litter was added 20.0 mL of cat urine, previously collected and pasteurized. The urine was aged to a greater degree as in EXAMPLES 1-3, so it contained a high level of odor from the $NH_3$. The flask was then stoppered with a 1-hole Neoprene stopper, through which was placed a Draeger tube sensitive to $NH_3$. The tubes were incubated at room temperature, and levels of $NH_3$ generated were checked throughout a one-day evaluation period. Sodium bentonite was also evaluated for comparison, except that 100.0 g of bentonite was used in the flask in order to represent about the same volume as the agglomerated litters. All trials were run in duplicate. Results are discussed for each zeolite as follows.

Comparison of Samples 1 and 2 (Mordenite)

Shown in FIG. 8 are plots of odor level in ppm $NH_3$ generated as a function of time for mordenite systems either treated with water and dried (sample 1) or treated with nanosilica and dried (sample 2) generated as a function of time. Note the time frame is in hours, due to the high level of odor produced in the aged urine. Results for bentonite are also shown in FIG. 8:

The system treated with nano silicate odor reducing agents exhibited a slightly lower level of odor throughout most of the time period compared with the water-treated system. Interestingly, bentonite exhibited lower levels of odor. The lower level of odor mitigation exhibited by mordenite compared with bentonite is probably related to the inherent properties of the zeolite, e.g., the channel area.

Comparison of Samples 3 and 4 (Faujasite)

Results comparing odor levels in samples 3 and 4 (with faujasite) are shown in FIG. 9. In this case, treatment with nanosilicate odor reducing agents did not net any benefit for odor mitigation, and the level of odor mitigation was worse compared with bentonite, and apparently much worse than in the examples with mordenite.

Comparison of Samples 5 and 6 (Chabazite)

Results for samples 5 and 6 (with chabazite) are shown in FIG. 10. In these results, chabazite systems showed superior odor mitigation performance compared with bentonite, and treatment of chabazite with nanosilica yielded superior performance to the water-treated system.

Conclusions and Possible Mechanistic Explanation

Data shown above and reported earlier showed that systems incorporating clinoptilolite, ferrierite, and chabazite all exhibited good odor mitigation performance, and treatment with nanosilica improved the performance. Mordenite showed slightly better odor mitigation performance, and treatment with silica enhanced the performance slightly more. For faujasite, however, odor mitigation performance was worse than bentonite, and treatment with nanosilicate odor reducing agents did not improve odor mitigation performance.

Without being bound by theory, it is possible that the ability of the zeolite to mitigate odor, and further be enhanced by treatment with nanosilicate odor reducing agent may be related to the channel size of the zeolite. In consider that the cross section of an ammonia ($NH_3$) molecule is about 3.5 Å (calculated from the associated van der Waals volume), cross sectional area ($\pi r^2$) of $NH_3$ can then be calculated to be 9.6 Å$^2$. We can then calculate the ratio of the channel area to $NH_3$ area as illustrated in TABLE 8.

TABLE 8

| Mineral | Channel Dimensions (Å) | Channel area (Å$^2$) | Channel area/ $NH_3$ area |
|---|---|---|---|
| Clinoptilolite | 3.9 × 5.4 | 21.1 | 2.2 |
| Ferrierite | 4.3 × 5.5 | 23.7 | 2.5 |
| Chabazite | 3.7 × 4.2 | 15.5 | 1.6 |

TABLE 8-continued

| Mineral | Channel Dimensions (Å) | Channel area (Å$^2$) | Channel area/ $NH_3$ area |
|---|---|---|---|
| Mordenite | 2.9 × 5.7 | 16.5 | 1.7 |
| | 6.7 × 7.0 | 46.9 | 4.9 |
| Faujasite | 7.4 | 54.8 | 5.7 |

For zeolites where the ratio was 2.5 or below (clinoptilolite, ferrierite, chabazite), odor mitigation was good, and the mitigation could be further enhanced with treatment with nanosilicate odor reducing agent. For faujasite, where the ratio was high (5.7), odor mitigation was poor, and treatment with nanosilicate odor reducing agent made no difference. Mordenite had two channel sizes, with ratios of 1.7 and 4.9, and indeed we saw an intermediate odor performance between those of the other zeolites. As such, it may be concluded that the efficacy of the zeolite to mitigate odor may be related to the channel size. Faujasite has a channel size that is much larger than the other zeolites, and showed a poorer efficacy against $NH_3$ odor. Therefore, selecting a zeolite-based liquid adsorbing material having a channel size that results in a ratio of 2.5 or below may be beneficial in reducing $NH_3$ odor when coated with a nanosilicate odor reducing agent.

Many modifications and other embodiments of the disclosure set forth herein will come to mind to one skilled in the art to which these disclosure pertain having the benefit of the teachings presented in the foregoing descriptions. Therefore, it is to be understood that the disclosure is not to be limited to the specific embodiments disclosed and that modifications and other embodiments are intended to be included within the scope of the appended claims Although specific terms are employed herein, they are used in a generic and descriptive sense only and not for purposes of limitation.

The invention claimed is:

1. An animal litter composition comprising:
   a zeolite-based liquid adsorbing material; and
   a nanosilicate odor reducing agent that reduces an odor of litter waste, the animal litter composition having a total nanosilicate odor reducing agent content of about 0.5% by weight to about 13% by weight based on the total weight of the animal litter composition;
   wherein the nanosilicate odor reducing agent is cationic.

2. The animal litter composition of claim 1, wherein the zeolite-based liquid adsorbing material comprises clinoptilolite, ferrierite, chabazite, mordenite, or a combination thereof.

3. The animal litter composition of claim 1, wherein the nanosilicate odor reducing agent reduces the odor of ammonia ($NH_3$).

4. The animal litter composition of claim 1, further comprising an additive material including a binder, a preservative, a biocide, a de-dusting agent, a fragrance, a bicarbonate, a clump aid, or a combination thereof.

5. The animal litter composition of claim 1, wherein the zeolite-based liquid adsorbing material defines channel dimensions having a channel area of 23.7 Å$^2$ or less.

6. The animal litter composition of claim 1, wherein the zeolite-based liquid adsorbing material defines a void volume of about 50% or less.

7. The animal litter composition of claim 1, wherein the zeolite-based liquid adsorbing material has a cation exchange capacity of 4.00 meq/g or less.

8. The animal litter composition of claim 1, wherein the nanosilicate odor reducing agent defines a plurality of particles, each particle having an approximate particle size of 22 nm or less.

9. The animal litter composition of claim 1, wherein the nanosilicate odor reducing agent is present as a coating on at least a portion of an outer surface of the zeolite-based liquid adsorbing material.

10. A method for producing an animal litter composition, the method comprising: providing a zeolite-based liquid adsorbing material; and coating the zeolite-based liquid adsorbing material with a nanosilicate odor reducing agent that reduces an odor of litter waste, said coating being sufficient to provide the animal litter composition with a total nanosilicate odor reducing agent content of about 0.5% by weight to about 13% by weight based on the total weight of the animal litter composition; wherein coating the zeolite-based liquid adsorbing material with the nanosilicate odor reducing agent comprises coating the zeolite-based liquid adsorbing material with a nanosilicate odor reducing agent that is cationic.

11. The method of claim 10, wherein providing the zeolite-based liquid adsorbing material comprises providing clinoptilolite, ferrierite, chabazite, mordenite, or a combination thereof.

12. The method of claim 10, wherein coating the zeolite-based liquid adsorbing material with the nanosilicate odor reducing agent comprises coating the zeolite-based liquid adsorbing material with a nanosilicate odor reducing agent that reduces the odor of ammonia ($NH_3$).

13. The method of claim 10, further comprising mixing the zeolite-based liquid adsorbing material with an additive material including a binder, a preservative, a biocide, a de-dusting agent, a fragrance, a bicarbonate, a clump aid, or a combination thereof.

14. The method of claim 10, wherein providing the zeolite-based liquid adsorbing material comprises providing a zeolite-based liquid adsorbing material defining channel dimensions having a channel area of 23.7 $Å^2$ or less.

15. The method of claim 10, wherein providing the zeolite-based liquid adsorbing material comprises providing a zeolite-based liquid adsorbing material defining a void volume of about 50% or less.

16. The method of claim 10, wherein providing the zeolite-based liquid adsorbing material comprises providing a zeolite-based liquid adsorbing material having a cation exchange capacity of 4.00 meq/g or less.

17. The method of claim 10, wherein coating the zeolite-based liquid adsorbing material with the nanosilicate odor reducing agent comprises coating the zeolite-based liquid adsorbing material with a nanosilicate odor reducing agent defining a plurality of particles, each particle having an approximate particle size of 22 nm or less.

18. The method of claim 10, wherein coating the zeolite-based liquid adsorbing material with the nanosilicate odor reducing agent comprises coating the zeolite-based liquid adsorbing material with the nanosilicate odor reducing agent on at least a portion of an outer surface of the zeolite-based liquid adsorbing material.

* * * * *